United States Patent [19]

Hewitt et al.

[11] Patent Number: 4,996,193

[45] Date of Patent: Feb. 26, 1991

[54] COMBINED TOPICAL AND SYSTEMIC METHOD OF ADMINISTRATION OF CYCLOSPORINE

[75] Inventors: Charles W. Hewitt, Orange; Kirby S. Black, Santa Ana, both of Calif.

[73] Assignee: The Regents of the University of California, Berkeley, Calif.

[21] Appl. No.: 318,676

[22] Filed: Mar. 3, 1989

[51] Int. Cl.$^5$ ............................................. A61K 37/02
[52] U.S. Cl. ................................. 514/11; 514/885; 514/886; 514/887
[58] Field of Search ................ 514/11, 825, 885, 886, 514/887

[56] References Cited

U.S. PATENT DOCUMENTS

| | | | |
|---|---|---|---|
| 3,288,824 | 11/1966 | Mahier et al. | 260/410.6 |
| 4,108,985 | 8/1978 | Ruegger et al. | 514/11 |
| 4,117,118 | 9/1978 | Harri et al. | 514/11 |
| 4,210,581 | 7/1980 | Ruegger et al. | 530/321 |
| 4,220,641 | 9/1980 | Traber et al. | 424/177 |
| 4,288,431 | 9/1981 | Traber et al. | 514/11 |
| 4,289,851 | 9/1981 | Traber et al. | 435/71 |
| 4,384,996 | 5/1983 | Bollinger et al. | 260/112.5 |
| 4,388,307 | 6/1983 | Cavanak | 424/177 |
| 4,396,542 | 8/1983 | Wenger | 260/112.5 |
| 4,553,974 | 11/1985 | Dewanjee | 8/94.11 |
| 4,554,351 | 11/1985 | Wenger | 544/177 |
| 4,639,434 | 1/1987 | Wenger et al. | 514/11 |
| 4,649,047 | 3/1987 | Kaswan | 424/78 |
| 4,677,968 | 7/1987 | Krueger | 128/898 |
| 4,681,754 | 7/1987 | Siegl | 424/10 |
| 4,703,033 | 10/1987 | Seebach | 514/11 |
| 4,764,503 | 8/1988 | Wenger | 514/11 |
| 4,771,122 | 9/1988 | Seebach | 530/317 |
| 4,839,342 | 6/1989 | Kaswan | 514/11 |
| 4,857,662 | 8/1989 | Satzinger et al. | 514/619 |

FOREIGN PATENT DOCUMENTS

| | | |
|---|---|---|
| 2019512 | 1/1987 | Japan . |
| 2019513 | 1/1987 | Japan . |
| 2207678 | 2/1989 | United Kingdom ............. 514/11 |

OTHER PUBLICATIONS

C. W. Hewitt et al., "Cyclosporine and Skin Allografts for the Treatment of Thermal Injury: I. Extensive Graft Survival with Low-Level Long-Term Administration and Prolongation in a Rat Burn Model", Transplantation 45: 13 (1988).

A. D. Hess et al., "Mechanisms of Action of Cyclosporine: Effect on Cells of the Immune System and on Subcellular Events in T Cell Activation", Transpl. Proc. 20: 29 (1988).

C. N. Ellis et al., "Cyclosporine Improves Psoriasis in a Double-Blind Study", JAMA 256: 3110 (1986).

L. H. Toledo-Pereyra et al., "Prolongation of Kidney Transplant Survival by Cyclosporine A Graft Pretreatment", Transplantation 33: 330 (1982).

R. D. Aldridge et al., "Inhibition of Contact Sensitivity Reactions to DNFB by Topical Cyclosporin Application in the Guinea-Pig", Clin. Exp. Immunol. 59: 23 (1985).

C. S. Lai et al., "Long-Term Survival of Skin Allografts in Rats Treated with Topical Cyclosporine", 44: 83 (1987).

(List continued on next page.)

*Primary Examiner*—Merrell C. Cashion, Jr.
*Assistant Examiner*—G. S. Kishore
*Attorney, Agent, or Firm*—Knobbe, Martens, Olson & Bear

[57] ABSTRACT

The present invention provides formulations for the topical application of cyclosporin to skin tissue for treatment of autoimmune, T-cell mediated immune disease, and inflammatory conditions, and for producing prolonged skin allograft survival and wound healing. In addition, methods for the use of said formulations—in tandem with systemic applications of cyclosporin or without same—are suggested. The present invention also suggests alternative formulations and delivery systems for the efficacious treatment of the aforementioned conditions, and further suggests a model with which formulations may be tested.

22 Claims, 1 Drawing Sheet

X. F. Zhao et al., "The Prolongation of Skin Allograft Survival by Topical Use of Cyclosporine A", Transpl. Proc. 20: 670 (1988).

E. Towpik et al., "Cyclosporine and Experimental Skin Allografts", Transpl. 40: 714 (1985).

Biren et al., "Prolonged Viability of Human Skin Xenografts in Rats by Cyclosporine", J. Invest. Dermatol. 86: 611 (1986).

M. Ried et al., "Cyclosporine Levels in Human Tissues of Patients Treated for One Week to One Year", Transpl. Proc. 15: 2434 (1983).

J. Thivolet et al., "Effects of Cyclosporin on Bullous Pemphigoid and Pemphigus", Lancet 1: 334 (1985).

J. I. Harper et al., "Cyclosporine for Psoriasis", Lancet 2: 981 (1984).

A. W. Thompson et al., "Topical Cyclosporin and Immunologically Mediated Skin Disorders", Lancet 1: 1212 (1987).

M. W. Mosteller et al., "Penetration of Topical Cyclosporine into the Rabbit Cornea, Aqueous Humor, and Serum", Arch Opthalmol 103: 101 (1985).

S. Levinger et al., "Effects of Systemic Administration of Chlorambucil and Topical Application of Cyclosporin A on Corneal Graft Survival in Rabbits", Isr. J. Med. Sci. 21: 670 (1985).

G. F. Babcock et al., "Prolongation of Skin and Graft Survival with Topical Immunosuppression", Seventh International Congress on Burn Injuries, Melbourne, Australia (Feb. 1986).

S. Shuster, "Cyclosporine in Dermatology", Transpl. Proc. 20: 19 (1988).

K. S. Black et al, "Transdermal Application of Cyclosporine Prolongs Skin Allograft Survival", Transpl. Proc. 20: 660 (1988).

C. A. Biren et al., "Dermatologic Applications of Cyclosporine", Arch Dermatol. 122: 1028 (1986).

R. D. Aldridge et al., "Cyclosporine and Skin Disease", Lancet 1: 160 (1985).

W. Muller et al., "Cyclosporin A for Psoriasis", NEJM 301: 555 (1979).

COMBINED TOPICAL AND SYSTEMIC METHOD OF ADMINISTRATION OF CYCLOSPORINE

BACKGROUND OF THE INVENTION

Cyclosporine (CsA), a selective immunosuppressant and a potent anti-inflammatory agent, has demonstrated great clinical success in inhibiting T-cell mediated immune processes such as allograft rejection, graft-versus-host disease, and autoimmune disease when administered systemically. (See, e.g., A. D. Hess al., *Transpl. Proc.* 20: 29 (1988).) As to the latter, systemic CsA has been proven efficacious for treating psoriasis autoimmune disorder of the skin. (See, e.g., C. N. Ellis, et al., *JAMA* 256: 3110 (1986).) However, the induction of tissue site and focal responding immunocytes could result in surprisingly greater efficacy, and could have significant immunologic and clinical ramifications.

As an example of the aforementioned ramifications, within the specialty of dermatology, it would be desirable to treat putative autoimmune conditions and related diseases of the skin, including, for example, eczema, contact hypersensitivity, alopecia areata and psoriasis. Few if any models for testing the disease mechanism and the efficacy of various treatment modalities have been available in this field, however. Moreover, due to the variability of expression of most skin conditions, and the inherent differences between epidermal tissues in various locations on the body, a single treatment methodology or pharmaceutical composition is rarely effective for all disease conditions presented.

A basic understanding of the immune response involved will facilitate the understanding and appreciation of the present invention. T-cell mediated immune events play an important role in eliciting allograft rejection and other inflammatory reactions. The immunological cascade that follows alloengraftment includes: (1) recognition of antigen; (2) lymphocyte activation; (3) development of specific cellular and molecular lines of communication between responding immunocytes via lymphokine release and induced expression of major histocompatibility complex ("MHC") antigens; and (4) mononuclear inflammatory cell infiltration into the target tissue which leads to eventual graft destruction (rejection). Systemic administration of CsA, a novel fungal metabolite, is well known to block this inflammatory cascade and to facilitate permanent allograft acceptance (actively-acquired immunological tolerance) in various experimental animal models, probably by inhibitory effects upon T-helper cells with sparing of cell expression. (See, e.g., A. D. Hess, et al., *Transpl. Proc.* 29 (1988).) Cyclosporins have novel immunosuppressive properties compared to conventional agents: they are selective in their mechanism of action, demonstrate superior graft survival times, and are potent anti-inflammatory compounds. Cyclosporins are well-recognized for their powerful ability to permanently alter immune responsiveness, in comparison with conventional agents, so that some degree of selective immunologic tolerance (graft acceptance) can be achieved in various models. Therefore, it would be extremely advantageous and desirable to develop topical formulations of cyclosporins for localized tissue site-specific action.

Conventionally, immunosuppressants have been administered at a systemic level in order to inhibit both cell- and humoral-mediated immune responses. However, the induction of localized site-specific immunosuppression could inhibit the mechanisms which lead to graft rejection and similar inflammatory immune processes operative in autoimmune and putative autoimmune disorders. Yet, a tissue site-specific immunosuppressive mechanism has not been conclusively demonstrated by local application of the cyclosporins.

More recently, the fungal metabolites known as cyclosporins, and particularly Cyclosporine A (CsA), have been established as the principal immunosuppressants in solid organ transplantations. The systemic use of cyclosporin prolongs the survival of experimental and clinical allografts, but continuing immunosuppressive therapy is generally necessary.

Yet, the long-term side effects of systemic administration of cyclosporins are of major concern. The related complications of nephrotoxicity and hepatotoxicity (i.e., kidney and liver damage), as well as an increase in infections, are a significant problem and may thus render treatment with cyclosporins inappropriate for certain patients, such as those who have been severely burned, or for those with skin conditions that are not life-threatening, such as psoriasis. One method for achieving indefinite survival of the graft or prolonged anti-inflammatory effects with CsA and for reducing its potentially toxic systemic side effects involves the localization of CsA in the target tissue.

For the purposes of clarity and easier comprehension, the terms "CsA", "Cyclosporine A" and "cyclosporine" may be considered interchangeable with the term "cyclosporin(s)" throughout this disclosure. While CsA is the cyclosporin typically used in most pharmaceutical preparations, the scope of this invention is not limited to this one type of cyclosporin.

Local inhibition of the rejection response with CsA has demonstrated mixed results. Perfusion of kidney allografts with CsA prior to transplantation did produce enhancement of tissue survival; however, prior, minimal systemic azathioprine immunosuppression was required. See, e.g., L. H. Toledo-Pereyra, et al., *Transplantation* 33: 330 (1982). Likewise, infusion of low-dose CsA into the ligated thoracic duct provided only a mild enhancement of rat kidney allograft survival. Delayed type hypersensitivity has been effectively inhibited in animals and man with topically-applied CsA (see, e.g., R. D. Aldridge, et al., *Clin. Exp. Immunol.* 59: 23, 1985), as has cornea allograft rejection. The topical application of CsA has also been shown to be effective in treating alopecia areata and contact hypersensitivity in humans, yet it appears to have no effect on psoriasis. Studies using topically-applied CsA demonstrated prolonged survival of rat skin allografts; see, e.g., C. S. Lai, et al., *Transplantation* 44: 83, 1987; X.F. Zhao, et al., *Transplant. Proc.* 20: 670 (1988). However, one such study concluded that most of the enhancement observed with local CsA treatment was due to the animals, ingestion of CsA from the treated area. See Zhao, supra. When means were taken to prevent the animals from ingesting CsA from the grafts, the investigators found that CsA blood levels were suboptimal (below 100 ng/ml) and negligible enhancement of skin allograft survival was seen. It has also been postulated that autoimmune disorders of the skin could benefit from transdermal (i.e., localized) treatment with CsA.

Thus, there is a need for topical and local formulations of cyclosporins, and a method for utilizing same, in the prevention of localized tissue site-specific inflammatory immune reactions. An example includes prevention of skin allograft rejection at a local level, but this would serve as a model for other inflammatory disorders such as autoimmune diseases of the skin (i.e., psoriasis, contact hypersensitivity, alopecia areata) and tissue or organ allografts. In particular, a methodology that locally provides allograft acceptance and attenuates T-cell mediated events is highly desirable. The present invention is directed to such a formulation and method of use.

SUMMARY OF THE INVENTION

The present invention exploits the observation that skin allograft survival may be prolonged via topical use of cyclosporins, and more particularly, Cyclosporine A. It is based on the concept that targeting CsA to a specific tissue is a desirable means for increasing efficacy and reducing systemic toxic concerns associated with this immunosuppressant. This localized effect of CsA also indicates potential usefulness in organ transplants, via perfusion and/or topical application. Further, cyclosporins may be effective in the clinical treatment of autoimmune skin disorders and other localized inflammatory reactions. In general, then, this treatment may be appropriate whenever there is a T-cell-mediated or mononuclear cellular inflammatory reaction incited by a fixed-tissue-based antigen and/or unknown mechanisms. In addition, local treatment of rheumatoid arthritis, multiple sclerosis, inflammatory lung disease, and other inflammatory disorders with cyclosporins may prove efficacious.

A critical mechanism for the induction of site-specific immune suppression by CsA appears to be the establishment of a systemic maintenance phase of immune non-responsiveness. To induce this maintenance state, an initial limited systemic dose of CsA appears necessary. Analogously, it is well-recognized that two distinct states of immunosuppression, the induction and maintenance phases, are important for the development of specific immune non-responsiveness. (See, e.g., E. Towpik, et al., *Transplantation* 40: 714 (1985).) It is not unlikely that CsA dosing requirements for efficacious site-specific suppression of autoimmune inflammatory skin disorders will underscore this observation. Continuous low-dose CsA administered systemically in conjunction with topical application may also prove efficacious.

In accordance with one aspect of the present invention, there is provided a method for utilizing local CsA in a topical formulation in conjunction with a short-term, limited systemic CsA schedule or a longer-term, low-dose systemic CsA schedule for effective abrogation of skin allograft rejection, T-cell mediated immune processes, and inflammatory reactions. This method should also prove effective in the clinical treatment of autoimmune skin disorders including psoriasis and other localized inflammatory reactions or cyclosporin-responsive conditions. One preferred embodiment suggests a systemically applied formulation wherein about 1 mg/kg/day to 15 mg/kg/day of cyclosporin is applied per single dosage.

In one embodiment, CsA is suspended in a topical cream formulation of a particular composition. In another embodiment, CsA is a component of a mineral oil-based topical formulation of a particular composition. In accordance with yet another embodiment of the invention, a topical formulation of cyclosporin is provided wherein CsA is embodied in a jojoba oil-based topical formulation of a particular composition. In accordance with other embodiments, the formulation is embodied in a paste, a gel, a liquid or a spray. Additionally, other embodiments include topical formulations of CsA in conjunction with different immunosuppressants and anti-inflammatory agents. Additional embodiments include formulations containing a preservative, as well.

For example, one preferred type of formulation according to the present invention may generally comprise cyclosporin, a pharmaceutical carrier, a co-solvent, a penetration enhancer, and an emulsifier. In a further embodiment, said components may be present in these approximate quantities: 5–80% pharmaceutical carrier; 5–50% co-solvent; 1–5% penetration enhancer; 0.1–20% emulsifier; and 0.2–25% cyclosporin (or cyclosporin applied to the tissue in such an amount that from about 0.5 mg/cm$^2$ to 5 mg/cm$^2$ of cyclosporin is applied per single dose).

Another preferred type of formulation according to the present invention may generally comprise, in approximate amounts by weight, 5–60% anhydrous lanolin; 5–60% mineral oil; 5–60% olive oil; 5–30% ethyl alcohol; 5–50% deionized water; 5–15% glycerol; 0.2–20% polysorbate 80; 1–5% polyvinylpyrrolidone; 0.2–25% cyclosporine A powder; and 0.1–10% sodium dodecyl sulfate.

Still another preferred type of formulation according to the present invention may generally comprise, in approximate amounts by weight, 5–60% anhydrous lanolin; 5–80% jojoba oil; 5–80% olive oil; 0.2–20% polysorbate 80; and 0.2–25% cyclosporine A powder.

An additional preferred type of formulation according to the present invention may generally comprise, in approximate amounts by weight, 5–60% anhydrous lanolin; 5–80% mineral oil; 5–80% olive oil; 0.2–20% polysorbate 80; and 0.2–25% cyclosporine A powder.

Another preferred type of formulation according to the present invention may generally comprise, in approximate amounts by weight, 5–60% anhydrous lanolin; 5–80% white petrolatum; 5–80% olive oil; 0.2–20% polysorbate 80; and 0.2–25% cyclosporine A powder.

Another preferred type of formulation according to the present invention may generally comprise, in approximate amounts by weight, 60–90% ethyl alcohol; 3–30% glycerol; 0.2–20% polysorbate 80; and 0.2–25% cyclosporine A powder.

According to the present invention, yet another example of a preferred formulation generally comprises, in approximate amounts by weight, 0–50% ethyl alcohol (v/v); 5–30% glycerol (v/v); 10–90% propylene glycol (v/v); and 0.2–25% cyclosporine A powder (w/v).

Another preferred type of formulation according to the present invention may generally comprise, in approximate amounts by weight, 0.2–20% polysorbate 80 (v/v); 2–30% ethyl alcohol (v/v); 5–50% deionized water (v/v); 5–40% glycerol (v/v); 10–80% propylene glycol (v/v); and 0.2–25% cyclosporine A powder (g/100 ml; w/v).

Another preferred type of formulation according to the present invention may generally comprise, in approximate amounts by weight, 0–20% ethanol (v/v); 0.2–25% cyclosporin (w/v); 19–80% white petrolatum (v/v); 0–10% heavy mineral oil (v/v); and 0.05–5% steroid powder (w/v). A further embodiment may utilize hydrocortisone as the steroid powder of choice.

Yet another preferred type of formulation according to the present invention may generally comprise cyclosporin and a pharmaceutically acceptable pharmaceutical carrier. Such a formulation may further comprise an esterification product of natural triglycerides and polyethylene glycol; a vegetable oil; and ethanol.

Another preferred type of formulation according to the present invention may generally comprise a formulation wherein the weight ratio of ester to cyclosporin is about 10: 0.2 to 10 parts by weight; vegetable oil is about 35 to 60% of the total composition by weight; and ethanol is about 1 to 20% of the total composition by weight. Further, such a formulation may generally include cyclosporin, wherein the cyclosporin is cyclosporin A powder in a concentration by weight of about 0.5% to about 25%.

In accordance with another aspect of the present invention, a dual skin graft model is provided, which may be used, for example, to test treatment protocols, such as the tandem treatment method suggested herein, or the topical administration of various cyclosporin-containing formulations.

Further, the present invention proposes that the use of pharmaceutically acceptable co-solvents and potential penetration promoters in cyclosporin-containing topical treatment formulations may result in decreased or lost efficacy locally, but increased efficacy systemically. Therefore, a gradient effect may be created by such formulations in the locally-treated tissues which extends into the systemic circulation. However, by lowering cyclosporin doses with such formulations, the potentially desired local result can be effected. In contradistinction, topical cyclosporin formulations without said co-solvents and obvious penetration promoters generally appear to facilitate deposition of the active agent locally in the treated tissues. These latter formulations are more effective at producing only localized effects without systemic involvement at equivalent cyclosporin concentrations.

In addition, it is suggested that various combinations of cyclosporins, steroids and other anti-inflammatory agents (non-steroidal agents, for example) be used in the local treatment of autoimmune and other inflammatory conditions to provide combined, additive, and/or synergistic efficacy.

In another embodiment of the present invention, alternative delivery systems, such as microencapsulation of cyclosporin-containing formulations within lipid membranous vesicles such as liposomes, are suggested.

Other embodiments of the present invention include the effective administration of CsA for systemic purposes via transdermal application. It is thought that this novel route of administration of CsA may provide new mechanisms of systemic action of CsA due to different metabolism when cyclosporin passes through the epidermis/dermis. These results also support the use of topical CsA formulations as an effective means for systemic delivery in patients needing immunosuppression but who may present compromised gastrointestinal absorption.

In addition, it is suggested, in another embodiment, that CsA may be administered locally to various tissues other than the skin; e.g., to the oral mucosa, the esophagus, the nasal septum, the bronchial tubes, and lung tissue, to name a few.

Moreover, CsA has been shown to have mild antifungal properties and topical application may be effective for fungal infections. Such application is suggested in another embodiment of the present invention.

Finally, the present invention proposes a method for utilizing any one of several topical CsA formulations in conjunction with systemically-applied CsA, or independently of same.

One advantage of the present invention over the prior art includes the fact that topical application of cyclosporin is effective in abrogating skin allograft rejection, inflammatory reactions and autoimmune skin disorders, without interfering with other cellular processes, apparently. As noted previously, other topically-applied formulations, such as those containing steroids, are less efficacious immunosuppressants, are less selective in their actions, and are less effective at inducing permanent immunologic tolerance than are cyclosporins. Further, in the case of steroid creams and ointments, a detrimental effect on wound healing and non-specific immunity against infection may result from their use.

A further advantage of the present invention is the fact that selectively delivering cyclosporin to a specific tissue targets the compound to responsive inflammatory cells and is a desirable means of increasing efficacy and reducing systemic toxic concerns associated with this immunosuppressant, in that the localized effect of cyclosporin indicates that it is potentially useful in organ transplants via topical application and/or via perfusion. Topical application of cyclosporin promotes allograft survival by delivering the compound to the target tissue, which facilitates the site-specific activity and efficacy of this immunosuppressant, while reducing potentially toxic systemic levels of cyclosporin.

Another advantage of the present invention is the fact that the dual skin allograft model provides an excellent research and clinical study protocol. For example, use of two allografts, one receiving treatment and the other left untreated, allows in vivo assessment of the systemic T-cell mediated response against the particular allograft in question. Since the treated allograft will potentially elicit systemic alloactivation, assessment of the test substance's ability to locally suppress these systemic alloaggressive cells will be possible. In addition, local effects of a test substance may be studied via the proposed dual skin allograft model.

Further advantages include the efficacy of the invention in treating a disease such as alopecia, where relatively normal skin is receiving treatment. In such instances, the required formulation is likely to be different from that which would effectively treat a more severe skin disorder such as psoriasis complicated by open lesions. In addition, dose and timing requirements will require study of the patient by the practitioner, and may necessitate variations for both systemic and topical phases of treatment.

Likewise, some conditions may require topical application alone, without prior systemic CsA treatment. Moreover, different formulations may easily be devised according to the protocols and methods set forth herein, to produce creams or ointments which may prove efficacious and advantageous.

DETAILED DESCRIPTION OF THE INVENTION

Figure 1:
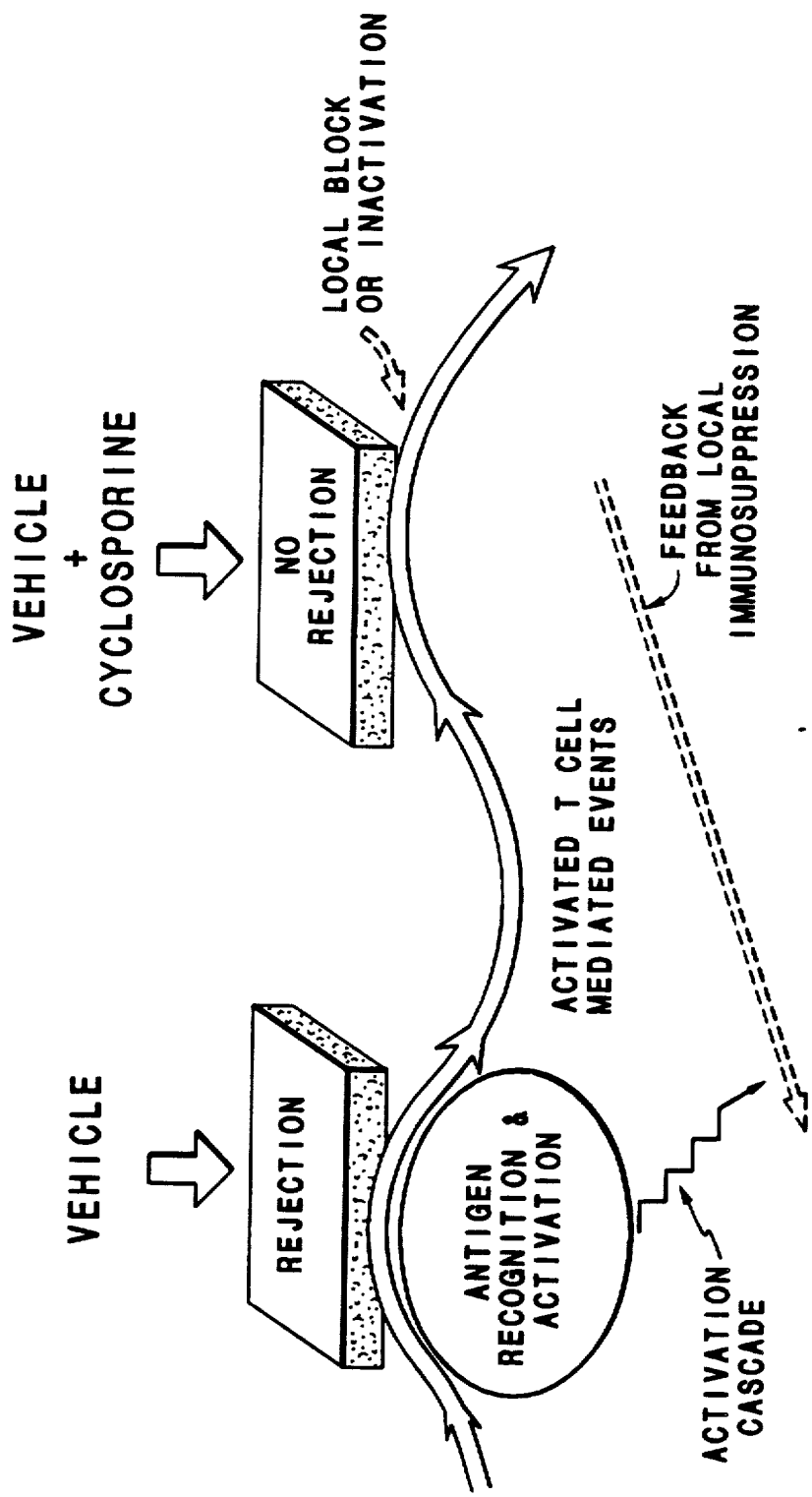
FIG. 1 is a graphic representation of the dual skin allograft model.

The present invention provides a method and compositions for abrogating skin allograft rejection and inflammatory reactions. It is based upon the observation that systemically-administered cyclosporin is an effective immunosuppressant in solid tissue or organ transplantation. The use of cyclosporin prolongs the survival of experimental skin allografts by delivering the drug to the target tissue and increasing efficacy, but systemic therapy alone can be excessively nephrotoxic, hepatotoxic and neurotoxic, and a concomitant increase in infections may pose a significant problem. Use of the present invention, however, circumvents these difficulties and provides a treatment methodology which effectively emphasizes the positive attributes of cyclosporin while minimizing the detrimental side effects.

A. Local Persistence Model

Conventionally, immunosuppressants have been administered at a systemic level in order to inhibit both cell- and humoral-mediated immune responses. However, the induction of localized site-specific immunosuppression could inhibit the mechanisms which lead to graft rejection and similar inflammatory immune processes operative in autoimmune and putative autoimmune disorders. Yet, a tissue site-specific immunosuppressive mechanism has not been conclusively demonstrated by local application of the cyclosporins.

Experimental results demonstrate definitive evidence for a site-specific immunosuppressive mechanism in the local application of CsA. T-cell mediated immunity was locally impaired. Several intriguing possibilities may be operative in the mechanism: specific blockade of lymphokine production; limiting expression of the major histocompatibility complex (MHC) determinants in the local tissue and T-cells circulating through the tissue site; and local site-specific suppressor cells may develop in the transplanted tissue. Even more impressive, however, is the consideration that topical application was efficacious at a time when the systemic immune response was obviously at a high level of alloaggression; this was evidenced by concomitant rejection of the vehicle-treated graft. This fact raises interesting questions regarding localized site-specific immune suppression by CsA. It would seem likely that local CsA application was not only effective for inhibiting primary cell-mediated inflammatory reactions, but also secondary cell-mediated immune responses if one assumes some circulating alloaggressive cells became primed to the untreated vehicle graft. (See FIG. 1.) This is somewhat surprising, since, in the prior art, CsA has been known to be less effective against an activated immune response. Conversely, it may be possible that some local suppressor cells developed in the graft undergoing topical administration since CsA is well known to facilitate suppressor cell development. These cells would then be available for systemic circulation to the contralateral vehicle graft and inhibition of a primary or an activated cell-mediated response.

These mechanisms may be more clearly investigated and illuminated via use of this model, as illustrated in FIG. 1. When considering the dual skin allograft model, it is important to note that the untreated allograft can act as a site for systemic immune recognition and alloactivation. As the inflammatory rejection cascade progresses, both cellular and humoral "arms" of the immune response can become involved. Activated T-cells and macrophages could then circulate systemically from the untreated contralateral graft to the locally-treated CsA allograft. The latter may then be subjected to pre-activated immune cells. Yet, the CsA-treated allografts demonstrated only minor changes during local CsA treatment. Therefore, it was shown that there were indeed site-specific immunosuppressive mechanisms operative. In addition, CsA is well-known to facilitate the generation of T-suppressor cells. It is possible that these cells could be induced at the local CsA site, then be available to circulate back to the untreated allograft, and provide some attenuation of the rejection process at the contralateral site.

B. Dual Skin Graft Model

The site-specific inflammatory model includes, for example, a dual partial-thickness skin allograft (e.g., 3 cm $\times$ 4 cm $\times$ 0.038 cm) from a Lewis X Brown Norway (LBN, $RT1^{1+n}$) donor to Lewis (LEW, $RT1^1$) rat recipient. These inbred strains are utilized because they are genetically homogeneous and well-defined, which eliminates the problems of unknown and uncontrolled variables. This model can also accommodate various strengths of genetic disparity via different combinations of donor/recipient pairs. For example, minor, major and even xeno-histocompatibility barriers can be utilized. Thus, the level of inflammatory reaction during rejection can be altered by the immunogenetic mismatch to model various degrees of inflammatory disease processes.

Using a further modification of this model, the human skin xenograft can be utilized to study pharmaceutically active agents and excipients as described previously, except with the use of dual grafts. (See, e.g., Biren, et al., *J. Invest. Dermatol.* 86: 611 (1986).)

Each recipient received two skin grafts: one anteriorly, and the other posteriorly, on the dorsal side. The skin allograft procedure used in the following Examples is based upon that described in Hewitt, et al., "Cyclosporine and Skin Allografts for the Treatment of Thermal Injury: I. Extensive Graft Survival With Low-Level Long-Term Administration and Prolongation in a Rat Burn Model," *Transplantation* 45:13 (1988), which is incorporated herein by reference.

The procedure essentially comprises the following: Ketamine (75 mg/kg, IM) and Acepromazine (2 mg/kg, IM) were used to anesthetize graft recipients and donors prior to surgery. The LBN-FI animals (donors) were anesthetized, shaven, their pelts (full thickness skin) surgically removed, and then sacrificed. The skin was cut to 0.038 cm thickness to yield a split thickness graft (using a Gibson Ross dermatome, Thackery Instruments, England) and was then placed into a saline-10% penicillin/streptomycin (combiotic) solution until applied to the recipient. The LEW rat was anesthetized and the skin excised to the subcutaneous fascia in the areas to be grafted. The dual 3 $\times$ 4 cm split thickness LBN skin allografts were applied and the wound edges were secured with 3–0 absorbable suture as well as application of stay sutures between the skin allograft and the underlying muscle bed. Immediately after grafting, each recipient received subcutaneous injections of systemic CsA at a dosage of 8 mg/kg/day for 10 days prior to transdermal application. Topical CsA was generally prepared at a concentration of 25 mg/ml in a vehicle as described in Section A above. The topical formulation of CsA (5 mg/kg/day) and its vehicle were applied to the CsA/vehicle and vehicle-only treated grafts, respectively. The treatments were randomly alternated between anterior and posterior grafts to eliminate potential bias due to anatomical location. Each graft was monitored and rated daily for erythema, desquamation, hair growth, and eschar, without knowledge of the regimen identity. Evidence of systemic cell-mediated immunosuppression was obtained by vitro lymphocyte mitogen stimulation responses using concanavalin A (Con-A) and phytohemagglutinin P (PHA-P). Assays were performed when rejection was seen in the vehicle-treated, but not the CsA-treated, allograft at approximately day 33. Blood lymphocytes were isolated by buffy coat centrifugation over Ficoll-Hypaque (Histopaque, Sigma Diagnostics, St. Louis, Mo.). Mononuclear cells from either experimental or LEW normal control animals were suspended in complete media containing RMPI1640 with Hepes (Irvine Scientific, Irvine, Calif.) supplemented with 10% fetal bovine serum (Hyclone, Logan, Utah), 1% penicillin/streptomycin (Sigma, St. Louis, Mo.) and 1% L-glutamate (Sigma). Cultures were made in 96well sterile round-bottom microtiter plates (Corning). Cultures were plated in triplicate and consisted of $2 \times 10^5$ responder lymphocytes in a total volume of 250 ul media. Con-A was added to a final media concentration of 4 ug/ml (20 ul). Some lymphocyte cultures were stimulated with PHA. In this case, the resulting final concentration of pHA-P (Rifco, Detroit, Mich.) in the media was 16 ug/ml (20ul). Background counts were determined from corresponding lymphocyte cultures which did not contain mitogen. Cells were cultured for 72 hours in a humidified environment with 5% $CO_2$. The wells were pulsed with 1.0 uCi of tritiated thymidine ($^3$H-TdR, ICN Pharm., Irvine, Calif.) 18 hours prior to harvesting (using MINI-MASH II, Microbiological Associates, Walkersville, Md.) The amount of radioactivity incorporated into the cells was determined as disintegration per minute (DPM) using the LS-1801 scintillation counter (Beckman, Fullerton, Calif.). Percent suppression was calculated from the following formula: 1-[(experimental DpM background DPM) (Lewis-normal control DPM—background DPM)].

Biopsies for histopathologic evaluation were obtained at day 55 (day of necropsy) for histopathologic examination. The tissues were fixed in 10% buffered formalin, sectioned at 8 u, and stained with hematoxylin and eosin. All skin tissue sections were read without knowledge of identity, to avoid any potential bias. Sections were examined for the presence of mononuclear cellular inflammatory infiltrates and architectural changes.

C. Application of Topical Cyclosporin

Our initial protocol involved the application of various topical formulations to skin allografts immediately post-operative. However, this resulted in apparent necrosis of the allografts, due either to the concentration of the vehicle or of CsA. We then applied the formulations to normal rat skin and found a slight erythemic reaction. We speculated that the solutions were slightly toxic to normal rat skin, but allografts appeared to be even more sensitive. This may be due to the persistence of unusual concentrations of the solution in the skin, as surgery apparently decreases the blood supply in the skin for a period of time.

In order to circumvent this problem, we administered systemic CsA at a dosage of 8 mg/kg/day for 10 days prior to topical application. This appeared sufficient to allow graft revascularization and resulted in optimal effectiveness with respect to topical application of CsA. Topical application of a dose equivalent to the systemic 8 mg/kg/day dosage from day 11 forward produced no detectable toxic reaction in the treated tissues. In contrast, the longevity of the treated allografts was significantly prolonged as compared to the controls, which did not receive topical CsA. As long as the topical CsA was applied, the skin grafts survived, grew hair, and appeared relatively normal. Our observations indicated that the grafts could have remained in maintenance phase graft acceptance as long as the topical application was continued. It is believed that these findings are directly transferable to, and applicable to, other inflammatory reactions, including autoimmune diseases of the skin. As the following Examples illustrate, however, combined systemic/topical treatment may not always be required. Either way, however, the proposed treatment may result in optimal efficacy for autoimmune and related disease conditions, as well as for allograft acceptance.

The cyclosporin formulated for use as the active ingredient in the topical compositions may be any cyclosporin and is not limited to CsA. Similarly, the amount of cyclosporin to be utilized in a formulation is not limited to a specific range and can be appropriately chosen based upon a desired effect, a particular form of the composition, penetration barriers, and the like. However, in view of its effect, it is generally preferable to formulate cyclosporin in the form of CsA in such an amount that 100 ml of the composition contains 0.2% to 25% or more of CsA (w/v).

Examples of substances which may be used as co-solvents in the illustrated embodiments include the following: ethanol; oleyl alcohol; alkylene polyols; glycerol; polyethylene glycol; oleic acids; vegetable oil PEG-6 complexes; caprylic triglyceride; capric triglyceride; glyceryl caprylate; glyceryl caprate; PEG-8 caprylate; PEG-8 caprate; ethoxydiglycol; and any mixture thereof.

Examples of substances which may be used as penetration enhancers in the illustrated formulations include the following: ethanol; oleyl alcohol; alkylene polyols; oleic acids; urea; pyrrolidones; surfactants such as sodium lauryl sulfate; vegetable oil PEG-6 complexes such as the commercially available Labrafils (Gattefosse, Elmsford, N.Y); caprylic/capric triglyceride (i.e., Labrafac Hydro, Gattefosse); glyceryl caprylate/caprate and PEG-8 caprylate/caprate (Labrasol, Gattefosse); and ethoxydiglycol (i.e., Transcutol, Gattefosse).; caprylic triglyceride; capric triglyceride; glyceryl caprylate; glyceryl caprate; PEG-8 caprylate; PEG-8 caprate; and any mixture thereof.

Examples of substances used as emulsifiers are selected from a group of self-emulsifying bases and consistency enhancers, including: PEG stearate and glycol stearate, PEG-6-32 stearate; PEG-6 stearate; and from a group of surfactants including: polysorbate 80, sodium lauryl sulfate, potassium methyl sulfate, potassium butyl sulfate, sodium tetrapropylene benzene sulfonate, dodecyl trimethyl ammonium chloride, lauric diethanolamide, cetrimide, cetomacrogol, and any mixture thereof.

Examples of substances used as other solvents or agents in which the CsA may be suspended include the following: anhydrous lanolin; white petrolatum; liquid petrolatum; olive oil; ethanol and ethanol-Tween 80 solutions; propylene glycol-water solutions; and jojoba oils.

Examples of substances used as self-emulsifying bases include the following: PEG stearate and glycol stearate (i.e., Tefose 63, Gattefosse); PEG-6-32 stearate (Tefose 1500, Gattefosse); PEG-6 stearate (Tefose 2000, Gattefosse); and other similar excipients.

The pharmaceutical carrier or diluent to be used in the present invention may be solid, semisolid or liquid. Such a pharmaceutical carrier may be a solvent, diluent, or carrier selected from the group consisting of waxes, cellulose derivatives, mineral oils, vegetable oils, petroleum derivatives, water, anhydrous lanolin, white petrolatum, liquid petrolatum, olive oil, ethanol and ethanol-polysorbate 80 solutions, propylene glycol-water solutions, and jojoba oils, methylcellulose or paraffin, beeswax, glyceryl stearate, PEG-2 stearate, propylene glycol stearate, glycol stearate, cetyl alcohol, stearyl alcohol, and any mixture thereof. There are also commercially available vehicles or carriers including Aquaphor ointment base (Beirsdorf Inc.), Eucerin creme/lotion (Beirsdorf), Acid Mantle (Sandoz), Nu-traderm creme/lotion (Owen), Vehicle/N or Vehicle/N Mild (Neutrogena), which may be used.

The compositions suggested herein may be prepared in a conventional form suitable for topical or local application such as an ointment, a paste, a gel, a spray, a liquid, and the like, via incorporating stabilizers, penetrants and the carrier or diluent with cyclosporin according to a known technique.

Likewise, some conditions may require topical application alone, without prior systemic CsA treatment. Moreover, different formulations may easily be devised according to the protocols and methods set forth herein, to produce creams or ointments which may prove efficacious and advantageous.

The following Examples further illustrate the present invention in detail but are not to be construed as limiting the scope of the invention.

EXAMPLE 1

(Use of the Tandem Treatment Protocol)

The site-specific inflammatory model includes a dual partial-thickness skin allograft (e.g., 3cm ×4cm ×.038 cm) from a Lewis X Brown Norway (LBN, RT1$^{1+n}$) donor to Lewis (LEW, RT1$^1$) rat recipient. Each recipient received two skin grafts: one anteriorly, and the other posteriorly, on the dorsal side. The skin allograft procedure was similar to that described in Hewitt, et al., (1988), cited supra. Cell culture, biopsy and fixation techniques were also as described above. The topical formulation applied was that identified below as the "Oleaginous Base Topical Formulation of Cyclosporin" (Example 2.c.).

Fixed tissue sections were examined for the presence of mononuclear cellular inflammatory infiltrates and architectural changes. A wide range of lesions were observed, but there was a clear disparity between the matched vehicle/control and locally-treated CsA grafts within each of the individual recipients. In general, vehicle grafts demonstrated severe mononuclear inflammatory infiltrates, necrosis, dermal fibrosis, hyperplasia of the epidermis, or even complete loss of the epidermis. There was clear evidence of rejection. At this time, the topically-treated CsA grafts demonstrated slight chronic mononuclear infiltrates, occasional areas of necrosis but absence of dermal fibrosis, and with fairly normal skin architecture preserved. Therefore, long after the initial signs of vehicle transplant rejection, histopathology confirmed a clear disparity between the control and CsA-treated grafts and a site-specific immunosuppressive mechanism in the observed skin allograft prolongation.

Percent graft survival was plotted over time, as measured by the first sign of erythema (redness), as shown in FIG. 1. This curve shows the disparity between matched CsA and vehicle-treated grafts with respect to initiation of the inflammatory response. It was interesting to note that although a minority of the experimental grafts demonstrated first signs of rejection (erythema only) during local treatment, the majority remained relatively normal by gross evaluation until the day of sacrifice (day 55–65).

Localized tissue levels of CsA were determined within both the vehicle- and CsA-treated grafts of each recipient at biopsy. Each graft sample (CsA- or vehicle-treated, approximately 200 ug tissue/sample) was weighed on an analytical balance and separately washed in olive oil, rinsed with saline, and frozen in liquid nitrogen. Each sample was then crushed, minced and ground in 4.0 ml of Tris buffer to solubilize the skin cells. The sample was clarified by centrifugation at 2500×g for 5 min. Supernatants were assayed for CsA by radioimmunoassay (RIA). The concentration of CsA was calculated per gram of tissue.

Systemic immune effects as measured by cyclosporin serum RIA levels demonstrated a hyperbolic curve that was asymptotic with zero. The levels rose to 2051±189 ng/ml at day 11 and dropped to 126±39 ng/ml by day 25 and were in the 40–70 ng/ml range from then on (68.7 on day 38). Cell-mediated immunity as assayed by mixed lymphocyte mitogen stimulation (Con-A and PHA-P) demonstrated that the animals' isolated lymphocytes were at least normal in their response if not stimulated (111.5±71.5% Con-A and 243.5 ± PHA-P of normal cell responses at day 31 with 100% being a normal response).

Site-specific immune effects as measured by local CsA values in the skin allografts demonstrated very high levels in the treated graft (37.5±25.3 ug/g) while the control 5 grafts demonstrated relatively low CsA levels (1.6±0.6 ug/g) at 36±2.3 days post operative. The CsA-treated graft contained 2629% more CsA than the vehicle-treated allograft, based on these values.

Local CsA administration until day 40 provided significantly enhanced graft survival compared to matched vehicle controls. Gross examination of the grafts revealed that the vehicle-treated allograft demonstrated the first sign of rejection (erythema) at a mean of 24.5±3.7 days, whereas the CsA- treated allograft demonstrated no clear signs of rejection up through day 55 (day of necropsy). The CsA-treated allograft also demonstrated more hair growth than the vehicle-treated allograft. The vehicle-treated grafts underwent vigorous rejection at this time.

The tissue CsA levels measured in this study correlate with previous studies. See, e.g., M. Ried, et al., Transp. Proc. 15: 2434 (1983). Levels have ranged from 10 ug/gm of skin after 21 days of oral CsA (10 mg/kg/day) administration in rats, to 1.7 ug/gm of CsA detected in human subjects during administration to those subjects.

The levels found in this study in the treated grafts (37 ug/gm±26 ug/gm) were over three times higher than those found to inhibit keratinocyte proliferation and langerhans cell antigen presentation, and were 21.5 times higher than in the vehicle-treated grafts. Yet, in this in vivo model, there were no gross indications of keratinocyte inhibition (i.e., wound healing and epidermal appearance were normal). Moreover, it appeared that there was no inherent toxicity to the treated tissues, despite the high level of CsA in the tissues. Although CsA tissue levels in the vehicle were 1.7 ug/gm, which seems relatively high, serum levels remained low (68 ng/ml) and were not sufficient to suppress systemic cell-mediated immune responsiveness as measured by the in vitro mitogen stimulation assays and by in vivo skin allograft rejection in the vehicle-treated graft.

EXAMPLE 2

(Suggested Topical Formulations of Cyclosporin)

As discussed supra, different conditions of the skin and other tissues will require different treatment modalities and formulations, in order to achieve maximum efficacy. Therefore, the following formulations are provided as examples of topical compositions that have proven to be efficacious in a site-specific fashion in our studies.

a. Creme-Lotion Base Topical Formulation of Cyclosporin.

One composition of topical cyclosporin is a water-in-oil creme emulsion and consists of the following ingredients:
25.40% Anhydrous Lanolin
18.20% Heavy Liquid Petrolatum (Mineral Oil)
18.20% Olive Oil
18.20% Ethyl Alcohol (EtOH, 200 proof)
9.10% Deionized Water
7.30% Glycerol
1.80% Tween 80
1.80% Polyvinylpyrrolidone (PVP)
4.54% CsA Powder (g/100 ml; w/v)
0.23% Sodium Dodecyl Sulfate (SDS) (g/ml; w/v)

The above ingredients should be mixed as follows. First, heat the olive oil to 60° C. and retain at this constant temperature. Slowly mix in the CsA powder to the olive oil solution with constant stirring. Continue mixing until CsA is completely dissolved, which may take up to two hours. Melt the lanolin with heat and maintain at 60° C. Mix PVP with liquefied lanolin at 60° C. Transfer the olive oil mixture into the CsA and maintain at a constant 60° C. temperature. Add the mineral oil and Tween 80 to the CsA mixture at a constant 60° C. temperature with continuous mixing. In a separate container, mix the SDS with EtOH and glycerol. Add this latter solution to the CsA mixture, and continue mixing at a constant 60° C. temperature until the solution is clear. Emulsify the cooled CsA solution with water by vigorous mixing at room temperature in order to create a creamy-textured solution. Transfer the solution into a labeled tube. The final concentration of CsA is, preferably, 45.45 mg/ml. Shake the tube well prior to application of the creme/lotion, and avoid re-heating.

b. Jojoba Oleaginous-Base Topical Formulation of Cyclosporin.

Another composition of topical cyclosporin represents a hydrophobic/lipophilic based formulation and may be synthesized from the following ingredients:
30% Anhydrous Lanolin
30% Jojoba Oil
30% Olive Oil
10% Tween 80
2.5% CsA Powder (g/100 ml; w/v)

The above ingredients may be mixed as follows. First, heat the jojoba oil to 60° C. and retain at this constant temperature. Slowly add in the CsA powder with constant stirring. Continue mixing until CsA is completely dissolved, which may take up to two hours. Melt the lanolin with heat and maintain it at 60° C. Mix the liquefied lanolin into the CsA-jojoba oil mixture and maintain same at a constant 60° C. temperature. Add the olive oil and Tween 80 at a constant 60° C. temperature with continuous mixing. Continue mixing until the solution is clear. Let the mixture cool and transfer same into a labeled tube. The final concentration of CsA is, preferably, 25 mg/ml.

c. Oleaginous Base Topical Formulation of Cyclosporin.

This topical formulation is a hydrophobic/lipophilic based formulation and consists of the following ingredients:
30% Anhydrous Lanolin
30% Heavy Liquid Petrolatum (Mineral Oil)
30% Olive Oil
10% Tween 80
2.5% CsA Powder (g/100 ml; w/v)

The above ingredients may be mixed as follows. Heat the olive oil to 60° C. and retain at this constant temperature. Slowly mix in the CsA powder accompanied by constant stirring. Continue mixing until CsA is completely dissolved, which may take up to two hours. Melt the lanolin with heat and retain at 60° C. Mix the liquefied lanolin into the CsA-olive oil mixture and maintain same at a constant 60° C. temperature. Add the mineral oil and Tween 80 at the constant 60° C. temperature with continuous mixing. Continue mixing the solution until it is clear. Let the mixture cool and transfer same into a labeled tube. The final concentration of CsA is, preferably, 25 mg/ml. Heating of this solution to 60° C. prior to use can provide increased solubilization of CsA following prolonged storage.

d. Oleaginous Base Ointment

This topical formulation represents a hydrophobic/lipophilic based ointment and consists of the following ingredients:
30% Anhydrous Lanolin
30% White Petrolatum
30% Olive Oil
10% Tween 80
2.5% CsA Powder (g/100 ml; w/v)

The above ingredients may be mixed as follows. Heat the olive oil to 60° C. and retain at this constant temperature. Slowly mix in the CsA powder accompanied by constant stirring. Continue mixing until CsA is completely dissolved, which may take up to two hours. Melt the lanolin with heat and retain at 60° C. Mix the liquefied lanolin into the CsA-olive oil mixture and maintain same at a constant 60° C. temperature. Add melted Petrolatum and Tween 80 at the constant 60° C. temperature with continuous mixing. Continue mixing the solution until it is clear. Let the mixture cool and transfer same into a labeled tube. The final concentration of CsA is, preferably, 25 mg/ml.

e. Hydrophilic. Water-Soluble Based Formulation #1

This topical formulation represents a hydrophilic, water-soluble based formulation and consists of the following ingredients:
80% Ethyl Alcohol
20% Glycerol
10% Tween 80
2.5% CsA Powder (g/100 ml; w/v)

The above ingredients may be mixed as follows. Dissolve CsA into the ethyl alcohol with constant stirring using a vortex. Add Tween 80 and then glycerol, and mix.

Our results demonstrated that this formulation is a hydrophilic, water-soluble base formulation of cyclosporin and appears stable over time. The ethanol and glycerol function as co-solvents and/or absorption promoters. However, results also demonstrate that, when this formulation is used in conjunction with a short-term limited systemic cyclosporin schedule (8mg/kg/d $\times$ 10 days), and at the topical dose specified, it is not effective in abrogating skin allograft rejection and inflammatory reactions. At a topical dose of 5 mg/kg/d, this formulation did not inhibit experimental or contralateral control skin allograft rejection. This is apparently related to graft tissue toxicity caused by the high levels of ethanol in the topical formulation. An eschar formed during the course of treatment which likely inhibited transdermal penetration and, in addition, was responsible for direct necrosis. These results provide strong support for the idea that local and/or systemic cyclosporin efficacy via local delivery can be dependent upon the vehicle or carrier composition.

f. Hydrophilic Water-Soluble Based Formula #2

This topical formulation represents a hydrophilic/-water-soluble based formulation and consists of the following ingredients:

0–10% Ethyl Alcohol (v/v)
30% Glycerol (v/v)
60–70% Propylene Glycol (v/v)
2.5% CsA Powder (g/100 ml; w/v)

The above ingredients may be mixed as follows. Constantly vortex the mixture throughout the procedure. Slowly dissolve CsA in the alcohol via constant agitation. Heat propylene glycol to 60° C. and mix into the CsA-alcohol solution. Lastly, add glycerol to the mixture, with constant agitation. The final concentration of topical CsA is, preferably, 25 mg/ml.

Our results demonstrated that the above formulation is a hydrophilic, water-soluble formulation of cyclosporin and appears stable over time. The propylene glycol functions as a co-solvent and absorption promoter. Our results also demonstrate that, when this formulation is used in conjunction with a short-term limited systemic cyclosporin schedule (8mg/kg/d $\times$ 10 days), and at the topical dose specified, it is effective in abrogating skin allograft rejection and inflammatory reactions.

At a topical dose of 5 mg/kg/d, this formulation effects both experimental and contralateral control skin allograft prolongation. At doses less than 5 mg/kg/d (i.e., 2.5 mg/kg/d), a local anti-inflammatory mechanism is operative and thus, only the experimentally-treated graft is prolonged. The former apparently occurs due to, at least partially, a systemic mechanism. This may be related to transdermal cyclosporin penetration into the systemic circulation. Additionally and/or alternatively, systemic anti-inflammatory effects may be faoilitated via the transdermal route by some undefined mechanism.

The hydrophilic nature, cyclosporin solubility, and/or absorption promotion due to propylene glycol in this formulation apparently enhanced transdermal penetration and is likely responsible for these systemic effects. The fact that a cyclosporin dose reduction effects a localized anti-inflammatory mechanism argues strongly in favor of a cyclosporin gradient being created in the target tissue which extended into the systemic circulation with this formulation.

This is in contradiction to results from some of the hydrophobic/lipophilic formulation experiments detailed herein. In the latter case, at equivalent topical cyclosporin doses, the agent appeared to localize primarily within the target tissue, thereby creating a depot, but did not extend significantly into the systemic circulation, or facilitate rapid transdermal penetration. These appeared to be advantageous features of the hydrophobic/lipophilic formulations with respect to achieving a localized anti-inflammatory mechanism.

These results tend to support that this hydrophilic formulation is an effective topical treatment for autoimmune skin disorders and other localized inflammatory reactions. These results also support use of this formulation as an effective means for systemic cyclosporin delivery at high doses in patients requiring immunosuppression, but who may present compromised gastrointestinal absorption. These results also provide strong support that local and/or systemic cyclosporin efficacy via local delivery can be dependent upon the vehicle or carrier composition, in addition to cyclosporin concentration.

g. Hydrophilic Water-Soluble Based Formula #3

This topical formulation is a hydrophilic/watersoluble based formulation which consists of the following ingredients:

2% Tween 80 (v/v)
10% Ethyl Alcohol (v/v)
20% Deionized Water (v/v)
28% Glycerol (v/v)
40% Propylene Glycol (v/v)
2.5% CsA Powder (g/100 ml; w/v)

The above ingredients may be mixed as follows. Constantly vortex the mixture throughout the procedure. Mix the Tween with the ethanol. Heat the mixture to 50° C. and maintain at this temperature. Slowly dissolve CsA in the Tween-ethanol by constant agitation. Heat the propylene glycol to 50° C. and mix into the CsA-ethanol solution. Add this glycerol mixture to the cyclosporin mixture, also with constant agitation. Cool to room temperature. Dispense into appropriate vials. The final concentration of topical CsA is, preferably, 25 mg/ml.

This formulation is an aqueous hydrophilic cyclosporin topical formulation using propylene glycol and glycerol as co-solvents and absorption promoters. Our results demonstrate that this formulation, when used in conjunction with a short-term limited systemic cyclosporin schedule (8mg/kg/day $\times$ 10 days) and at the topical dose specified, is effective in abrogating skin allograft rejection and inflammatory reactions. Our results also demonstrate that this formulation is a soluble formulation of cyclosporin and appears stable over time.

At a topical dose of 5 mg/kg/d, this formulation effects experimental and partial contralateral control skin allograft prolongation. Inflammatory alterations (erythema) are observed in the control vehicle-treated grafts which do not progress to complete rejection. However, a local anti-inflammatory mechanism is also operative. Thus, only the experimentally treated graft is prolonged without any evidence of inflammation. Therefore, and most interestingly, evidence for both local and systemic anti-inflammatory mechanisms is presented with this formulation. This may be related to partial transdermal cyclosporin penetration into the systemic circulation. Additionally and/or alternatively, systemic anti-inflammatory effects may be facilitated via the transdermal route by some undefined mechanism.

The hydrophilic nature, cyclosporin solubility, and/or absorption promotion due to propylene glycol in this formulation apparently enhanced transdermal penetration and is likely responsible for the partial systemic effects.

However, the local anti-inflammatory effect may be due to partial inhibition of rapid transdermal penetration and more effective localization. This may possibly be related to the aqueous nature of the formulation and reduced cyclosporin solubility in comparison to other hydrophilic compositions detailed herein. These results support this formulation as an effective topical treatment of autoimmune skin disorders and other localized inflammatory reactions. These results also provide strong support of the idea that local and/or systemic cyclosporin efficacy via local delivery can be dependent upon the vehicle or carrier composition, and upon cyclosporin concentration.

h. Oleaginous Base Cyclosporin Topical Formulation

This formulation is advantageous for topical and dermal application due to its hydrophilic/lipophilic balance. This formulation may be prepared according to U.S. Pat. No. 4,388,307, which describes liquid pharmaceutical compositions of cyclosporin for drink solutions, and for oral and parenteral administration. The liquid pharmaceutical composition used herein, which has been adapted for topical use, comprises CsA and a carrier consisting of the following: (1) An esterification product, trade name Labrafil (Labrafil M 1944 CS, Gattefosse, Elmsford, N.Y.) of natural triglycerides and polyethylene glycol which may be prepared according to U.S. Pat. No. 3,288,824; (2) a vegetable oil; and (3) ethanol.

The preferred embodiment contains ester to cyclosporin in a weight ratio of about 10:0.2 to 10 parts by weight; vegetable oil is 35 to 60% of the total composition by weight; and ethanol is 1 to 20% of the total composition by weight.

For example, a formulation may be mixed as follows: a liquid pharmaceutical composition of cyclosporin (e.g. Sandimmune Oral Solution, Sandoz Ltd., Basel, Switzerland) is diluted to 25 mg/ml in its carrier (1 part Sandimmune to 3 parts carrier, vol/vol). The carrier consists of: (1) a stirred mixture of Labrafil M 1944 CS and absolute ethanol (40:15 w/w); (2) olive oil is then added to this mixture in the ration of 0.4 to 1 ml (olive oil to ethanol-Labrafil, v/v). The carrier solution is then filtered.

Our results demonstrate that this formulation, when used in conjunction with a short-term limited systemic cyclosporin schedule (8 mg/kg × 10 days), and at the topical dose specified, is effective in abrogating skin allograft rejection and inflammatory reactions. At a topical dose of 5 mg/kg/d, this formulation effects both experimental and contralateral control skin allograft prolongation. At doses less than 5 mg/kg/d (i.e., 2.5 mg/kg/d), only a local anti-inflammatory mechanism is operative and thus, only the experimentally-treated graft is prolonged. The former apparently occurs due in part to a systemic mechanism. This may be related to transdermal cyclosporin penetration into the systemic circulation. Additionally and/or alternatively, systemic antiinflammatory effects may be facilitated via the transdermal route by some undefined mechanism.

The hydrophilic/lipophilic balance, cyclosporin solubility, and/or absorption promotion with this formulation apparently allowed enhanced cyclosporin penetration transdermally. It is known that the amphipathic nature of the Labrafils allows enhanced penetration of active ingredients through skin in comparison to conventional oily carriers, and therefore is likely part of the mechanism of the former. It is likely that this is responsible for the observed systemic effects. The fact that a cyclosporin dose reduction effects a localized anti-inflammatory mechanism argues strongly for a cyclosporin gradient being created in the target tissue which extended into the systemic circulation with this formulation. This is in contradistinction to results from some of the more hydrophobic/lipophilic formulation experiments detailed herein. In the latter cases, at equivalent topical cyclosporin doses, the agent appeared to primarily localize within the target tissue, did not extend significantly into the systemic circulation, or facilitate rapid transdermal penetration. These appeared to be advantageous features of the hydrophobic/lipophilic formulations with respect to achieving a localized anti-inflammatory mechanism.

EXAMPLE 3

(Combined Treatments)

Cyclosporins may be used in conjunction with steroids and other anti-inflammatory or immunosuppressive agents, such as hydrocortisone, betamethasone dipropionate, indomethacin and azathioprine, to name but a few, in order to facilitate and possibly synergize the treatment of inflammatory diseases of the skin and to promote wound healing. Such topical formulations may also be used in conjunction with systemic treatment, albeit the systemic/topical treatment modality is not required for said topical formulations to prove efficacious.

For example, in the case of a disease such as alopecia, where relatively normal skin is receiving treatment, the required formulation is likely to be different from that which would effectively treat a more severe skin disorder such as psoriasis complicated by open lesions. In addition, dose and timing requirements will require study of the patient by the practitioner, and may necessitate variations for both systemic and topical phases of treatment.

a. Steroid-Cyclosporin Topical Formulation

This topical formulation consists of the following ingredients:
7% Ethanol (v/v)
25% Sandimmune Oral Cyclosporin (100mg/ml) Solution (v/v)
60% White Petrolatum (v/v)
8% Heavy Mineral Oil (v/v)
1.0% Hydrocortisone Powder (g/100ml: w/v)

The above ingredients may be mixed as follows. Dissolve hydrocortisone in the ethanol by constant agitation for approximately 10 min. It will remain incompletely soluble. Add this mixture with constant agitation to the Sandimmune solution and heat to approximately 60° C. for 5 min. Ethanol in this ratio is fully, and hydrocortisone partially, soluble in the Sandimmune solution, respectively. Charge the mineral oil to this solution with agitation. In a separate container, melt the petrolatum by heating it to 60° C. Mix with vigorous and continuous agitation. Let cool to room temperature. Continue agitating to effect even dispersion of the hydrocortisone until solidified. The final concentration of CsA is, preferably, 25 mg/ml. The final concentration of hydrocortisone is, preferably, 10 mg/ml.

This formulation is a novel, topical oleaginous, hydrophobic/lipophilic ointment base comprising the combined active ingredients of cyclosporin and a steroid—for example, hydrocortisone. Our results demonstrate that two classes of potent anti-inflammatory agents, cyclosporins and steroids, can successfully be combined in a topical formulation to potentially enhance efficacy. This topical formulation was proven to be efficacious in producing a site-specific localized anti-inflammatory effect and significantly enhanced graft survival compared to matched vehicle-treated controls.

The formulation is advantageous for topical and dermal application due to the chemical properties and hydrophilic/lipophilic balance of the liquid Sandimmune vehicle. The liquid pharmaceutical composition preferably comprises CsA and a carrier consisting of the following: (1) an esterification product (e.g. Labrafil) of natural triglycerides and polyethylene glycol which may be prepared according to U.S. Pat. No. 3,288,824; (2) a vegetable oil; and (3) ethanol.

With heating, and due to the carrier vehicle's chemical properties, hydrocortisone can be partially solubilized independent of prior solubilization in ethanol. Therefore, the solubility of hydrocortisone in ethanol, miscibility of ethanol in the Sandimmune vehicle, and partial hydrocortisone solubility in the vehicle alone serves to facilitate the combination of the two active ingredients in a single topical formulation.

Examples of other steroidal agents that could analogously be combined with cyclosporin(s) in a single topical formulation in order to potentially enhance efficacy include, but are not limited to, the following: betamethasone dipropionate; betamethasone valerate; fluocinolone acetonide; triamcinolone acetonide; prednisone; methylprednisolone; and prednisolone.

b. Anti-Inflammatory Agents and Cyclosporin

Examples of non-steroidal anti-inflammatory agents that could analogously be combined with cyclosporins in a single topical formulation in order to potentially enhance efficacy include, but are not limited to: indomethacin; sulindac; ibuprofen; aspirin; naproxen; and tolmetin.

c. Immunosuppressive Agents and Cyclosporin

Examples of immunosuppressive agents that could analogously be combined with cyclosporin(s) in a single topical formulation in order to potentially enhance efficacy include, but are not limited to, the following: azathioprine; cyclophosphamide; the macrolide FK-506; deoxyspergualin; bredinin; didemnin B; methotrexate; and thalidomide.

What is claimed is:

1. A method for treating T-cell mediated immune processes, allograft rejection, inflammations, autoimmune conditions or cyclosporin-responsive conditions in animals, comprising: topically applying a formulation containing cyclosporin in pharmaceutically effective amounts to the affected tissue; and systemically administering a formulation containing cyclosporin in pharmaceutically effective amounts in conjunction with said topical application.

2. A method according to claim 1, further comprising: initiating said systemic administration prior to said administration of topical cyclosporin, and discontinuing said systemic administration prior to discontinuing said topical administration.

3. A method according to claim 1, further comprising: initiating said systemic administration at a first dosage level prior to initiating said topical administration, and lowering said systemic dosage to a second level during said topical administration.

4. A method according to claim 2 or 3, wherein the topically-applied formulation comprises from about 0.2% to 25% cyclosporin by weight, and is applied to the tissue in such an amount that from about 0.5 mg/cm$^2$ to 5 mg/cm$^2$ of cyclosporin is applied per single dose, and further, wherein the systemically-applied cyclosporin-containing formulation is applied in such an amount that from about 1 mg/kg/day to 15 mg/kg/day of cyclosporin is applied per single dosage.

5. A method according to claim 4, wherein the topically-applied formulation contains from about 0.5% to 15% cyclosporin, by weight.

6. A method according to claim 5, wherein the topically-applied formulation containing cyclosporin further comprises one or more of the following:
a pharmaceutical carrier;
a co-solvent;
a penetration enhancer; and
an emulsifier.

7. A method according to claim 6, wherein the pharmaceutical carrier is a solvent, diluent, or carrier selected from the group consisting of waxes, cellulose derivatives, mineral oils, vegetable oils, petroleum derivatives, water, methylcellulose or paraffin, beeswax, glyceryl stearate, PEG-2 stearate, propylene glycol stearate, glycol stearate, cetyl alcohol, steryl alcohol and other similar agents, anhydrous lanolin, white petrolatum, liquid petrolatum, olive oil, ethanol, ethanol-polysorbate 80 solutions, propylene glycol-water solutions, and jojoba oils, and any mixture thereof.

8. A method according to claim 6, wherein the co-solvent is selected from the group consisting of ethanol; oleyl alcohol; alkylene polyols; glycerol; polyethylene glycol; oleic acids; vegetable oil PEG-6 complexes; caprylrc triglyceride; capric triglyceride; glyceryl caprylate; glyceryl caprate; PEG-8 caprylate; PEG-8 caprate; ethoxydiglycol; and any mixture thereof.

9. A method according to claim 6, wherein the penetration enhancer is selected from the group consisting of ethanol; oleyl alcohol; alkylene polyols; oleic acids; urea; pyrrolidones; surfactants; vegetable oil PEG-6 complexes; caprylic triglyceride; capric trrglyceride; glyceryl caprylate; glyceryl caprate; PEG-8 caprylate; PEG-8 caprate; ethoxydiglycol; and any mixture thereof.

10. A method according to claim 6, wherein the emulsifier is selected from a group consisting of PEG stearate and glycol stearate, PEG-6-32-stearate; PEG-6 stearate; polysorbate 80, sodium lauryl sulfate, potassium methyl sulfate, potassium butyl sulfate, sodium tetrapropylene benzene sulfonate, dodecyl trimethyl ammonium chloride, lauric diethanolamide, cetrimide, cetomacrogol, and any mixture thereof.

11. A method according to claim 6, wherein the topical formulation is an ointment.

12. A method according to claim 6, wherein the topical formulation is a paste.

13. A method according to claim 6, wherein the topical formulation is a gel.

14. A method according to claim 6, wherein the topical formulation is a cream.

15. A method according to claim 6, wherein the topical formulation is a liquid.

16. A method according to claim 15, wherein the topical formulation is a spray.

17. A method according to claim 6, wherein the topical formulation comprises, in approximate amounts by weight:
   a. 5-80% pharmaceutical carrier;
   b. 5-50% co-solvent;
   c. 1-5% penetration enhancer;
   d. 0.1-20% emulsifier; and
   e. 0.2-25% cyclosporin.

18. A method according to claim 17, wherein the cyclosporin is Cyclosporine A powder.

19. A method for inducing acceptance of organ or tissue transplants by an animal host organism, comprising:
   a. systemically administering a formulation containing cyclosporin in pharmaceutically effective amounts, to the host organism;
   b. topically administering a formulation containing cyclosporin in pharmaceutically effective amounts to the transplanted or grafted tissue or organ, subsequent to said systemic treatment; and
   c. continuing the topical administration until the graft or transplant has been accepted by the host.

20. A method according to claim 19, further comprising: initiating said system administration at the time of allografting and discontinuing said systemic administration once wound healing has occurred.

21. A method according to claim 1 or claim 19, wherein said animal is a mammal.

22. A method according to claim 21, wherein said mammal is a human.

* * * * *